(12) United States Patent
Bhat et al.

(10) Patent No.: US 10,275,875 B2
(45) Date of Patent: Apr. 30, 2019

(54) METHOD AND DEVICE FOR DYNAMIC EFFECTS CORRECTION IN MEDICAL IMAGING

(71) Applicant: SIEMENS HEALTHCARE GMBH, Erlangen (DE)

(72) Inventors: Himanshu Bhat, Newton, MA (US); Thorsten Feiweier, Poxdorf (DE); Tobias Kober, Lausanne (CH); Carsten Prinz, Baiersdorf (DE); Daniel Nico Splitthoff, Erlangen (DE); Stephan Stoecker, Baiersdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 294 days.

(21) Appl. No.: 15/092,843

(22) Filed: Apr. 7, 2016

(65) Prior Publication Data
US 2016/0300353 A1 Oct. 13, 2016

(30) Foreign Application Priority Data

Apr. 7, 2015 (EP) .................................. 15162610

(51) Int. Cl.
*G06T 7/00* (2017.01)
*G01R 33/565* (2006.01)
(Continued)

(52) U.S. Cl.
CPC ...... *G06T 7/0012* (2013.01); *G01R 33/56509* (2013.01); *G06T 7/20* (2013.01);
(Continued)

(58) Field of Classification Search
CPC ............. G06T 7/20; G06T 2207/10088; G06T 2207/10092; G06T 2207/10096;
(Continued)

(56) References Cited

U.S. PATENT DOCUMENTS

2005/0033156 A1* 2/2005 Kruger ................. G01R 33/243
600/410
2005/0203373 A1* 9/2005 Boese .................... A61B 6/481
600/407
(Continued)

FOREIGN PATENT DOCUMENTS

WO  WO 0184172 A1 * 11/2001 ......... G01R 33/5676
WO  2007106360 A1    9/2007

OTHER PUBLICATIONS

Santos J.M. et al.: "Flexible Real-Time Magnetic Resonance Imaging Framework"; Proceedings of the 26th Annual Conference of the IEEE EMBS; San Francisco; CA, USA; vol. 3; pp. 1048-1051; XP010774954; DOI: 10.1109/IEMBS.2004.1403343; ISBN: 978-0-7803-8439-2 / Jan. 9, 2004.
(Continued)

*Primary Examiner* — Amanda Lauritzen Moher
*Assistant Examiner* — Chao Sheng
(74) *Attorney, Agent, or Firm* — Laurence Greenberg; Werner Stemer; Ralph Locher

(57) ABSTRACT

A method for automatically and dynamically optimizing image acquisition parameters/commands of an imaging procedure performed by a medical imaging apparatus in order to mitigate or cancel dynamic effects perturbing the image acquisition process of an object to be imaged by the medical imaging apparatus. The method includes connecting a dynamic correction module (DCM) to the medical imaging apparatus, automatically acquiring by the DCM image acquisition parameters/commands and data about dynamic changes or effects, and automatically determining in real time, by the DCM, at least one new image acquisition parameter/command from the image acquisition parameters/commands defined in the imaging control system and the dynamic change data, while the image acquisition parameter/command defined in the imaging control system
(Continued)

remains unchanged. The method further includes automatically providing, by the DCM, the new image acquisition parameter/command to the hardware control system.

13 Claims, 1 Drawing Sheet

(51) Int. Cl.
| | | |
|---|---|---|
| G06T 7/20 | (2017.01) | |
| H04N 5/232 | (2006.01) | |
| H04N 5/357 | (2011.01) | |
| G06T 7/80 | (2017.01) | |
| A61B 5/055 | (2006.01) | |
| A61B 8/08 | (2006.01) | |
| A61B 6/00 | (2006.01) | |
| G01R 33/54 | (2006.01) | |

(52) U.S. Cl.
CPC ............ *G06T 7/80* (2017.01); *H04N 5/23203* (2013.01); *H04N 5/23216* (2013.01); *H04N 5/357* (2013.01); *A61B 5/055* (2013.01); *A61B 6/5264* (2013.01); *A61B 8/5276* (2013.01); *G01R 33/543* (2013.01); *G01R 33/56563* (2013.01); *G06T 2207/10088* (2013.01)

(58) Field of Classification Search
CPC .......... G01R 33/56509; G01R 33/5673; G01R 33/565; G01R 33/563; G01R 33/543; G01R 33/56; A61B 8/5276; A61B 8/5264; A61B 8/05
See application file for complete search history.

(56) References Cited

U.S. PATENT DOCUMENTS

| | | | | |
|---|---|---|---|---|
| 2007/0253599 | A1* | 11/2007 | White | G01R 33/56509 |
| | | | | 382/107 |
| 2007/0280508 | A1* | 12/2007 | Ernst | A61B 5/055 |
| | | | | 382/107 |
| 2008/0226149 | A1* | 9/2008 | Wischmann | A61B 6/503 |
| | | | | 382/131 |
| 2009/0116761 | A1* | 5/2009 | Wheaton | A61B 5/055 |
| | | | | 382/254 |
| 2009/0209846 | A1 | 8/2009 | Bammer | |
| 2012/0268124 | A1 | 10/2012 | Herbst et al. | |

OTHER PUBLICATIONS

Zaitsev M. et al.:"Magnetic resonance imaging of freely moving objects: Prospective real-time motion correction using an external optical motion tracking system"; NeuroImage; Academic Press; Orlando, FL; USA; vol. 31; No. 3; pp. 1038-1050; XP024906396; ISSN: 1053-8119; DOI:10.1016/J.NEUROIMAGE.2006.01.039 / Jan. 7, 2006.

White N. et al: "PROMO: Real-Time Prospective Motion Correction in MRI Using Image-Based Tracking"; Magnetic Resonance in Medicine; John Wiley & Sons; Inc. US; vol. 63; No. 1; pp. 91-105; XP007916079; ISSN: 3740-3194 / Jan. 1, 2010.

Dold C. et al.: "Advantages and Limitations of Prospective Head Motion Compensation for MRI Using an Optical Motion Tracking Device"; Academic Radiology, Reston , VA, US; Vo. 13; No. 9; pp. 1093-1103; XP028012632; ISSN: 1076-6332; DOI:10.1016/J.ACRA.2006.05.010; / Jan. 9, 2006.

Aksoy M. et al.: "Real-Time Optical Motion Correction for Diffusion Tensor Imaging"; Magnetic Resonance in Medicine; vol. 66; No. 2; pp. 366-378; XP055031759; ISSN: 0740-3194, DOI: 10.1002/mrm.22787 / Mar. 22, 2011.

* cited by examiner

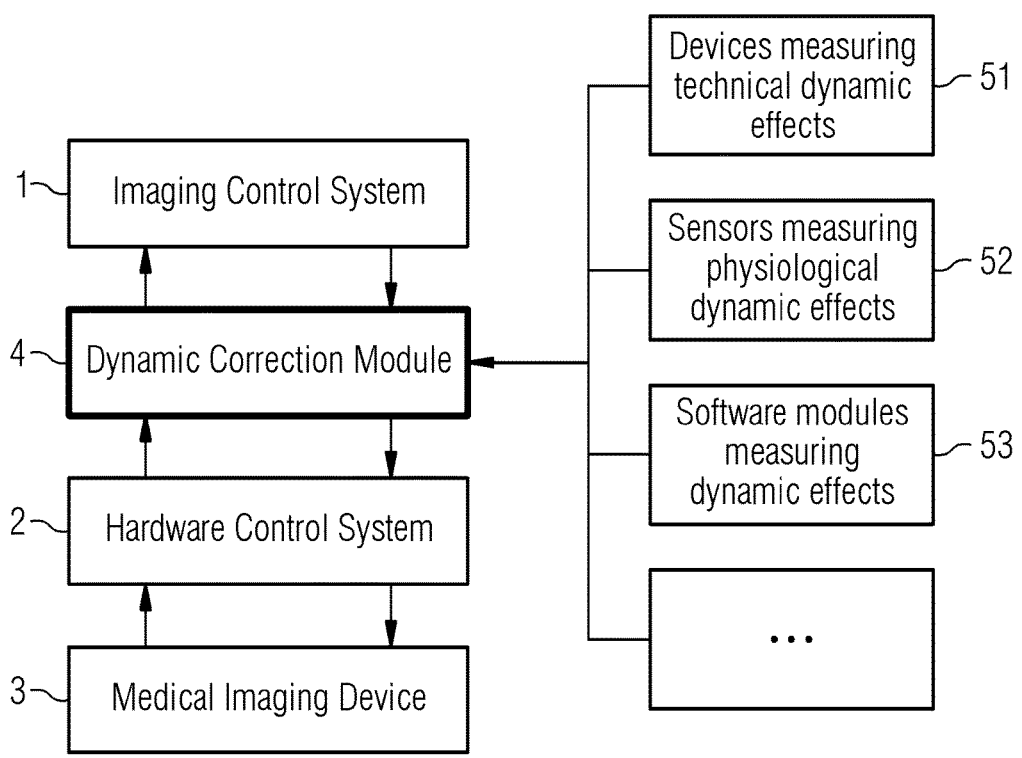

METHOD AND DEVICE FOR DYNAMIC EFFECTS CORRECTION IN MEDICAL IMAGING

CROSS-REFERENCE TO RELATED APPLICATION

This application claims the priority, under 35 U.S.C. § 119, of European application EP 15 162 610.8, filed Apr. 7, 2015; the prior application is herewith incorporated by reference in its entirety.

BACKGROUND OF THE INVENTION

Field of the Invention

The present invention relates generally to the correction of arte facts appearing in images obtained by a medical imaging apparatus and coming from dynamic effects occurring during imaging of an object by the medical imaging apparatus.

It is well known by people skilled in the art that the effect of object motion when imaging an object by for example of MRI techniques is a common problem which frequently degrades the quality of the MRI image of the object. It can be motion of the object itself or motion of a part, e.g. an internal part, of the object. More generally, effects changing the environment during the imaging process of an object to be imaged, like object motion or changes in the technical environment, are referred to as "dynamic effects". The dynamic effects have the disadvantage of degrading the image quality of the resulting images notably by creating image arte acts, which might hamper clinical diagnosis or yield the need for rescanning the object, thus increasing healthcare costs and impeding patient comfort.

Several means to correct dynamic effects exist, aiming at mitigating the resulting image arte facts. Some of the techniques try to improve the images a posteriori (retrospectively), others try to change imaging parameters as, for example, the field-of-view (FOV) already during the medical image acquisition. Retrospective techniques which try to correct data impeded by the effects after they were acquired have the advantage to have minimal or no impact on the imaging process itself, but are unfortunately limited since some arte facts are not correctable a posteriori. Prospective correction methods, on the other hand, can adapt imaging parameters dynamically during the acquisition. They typically require, however, considerable changes in the medical imaging control software or hardware.

SUMMARY OF THE INVENTION

An objective of the invention is to provide a method and a device for automatically and dynamically optimizing image acquisition parameters and/or image acquisition commands (hereafter "image acquisition parameters/commands"—more generally, "x/y" means in the present patent application "x and/or y") of an imaging procedure performed by a medical imaging apparatus in order to mitigate arte facts resulting from dynamic effects occurring during image acquisition.

The objective is achieved according to the present invention with respect to a method, in particular a computer-implemented method, for automatically and dynamically optimizing image acquisition parameters and/or image acquisition commands of an imaging procedure performed by a medical imaging apparatus, e.g. a magnetic resonance imaging (MRI) apparatus, in order to mitigate or cancel dynamic effects perturbing the image acquisition process of an object (or subject) to be imaged by the medical imaging apparatus. The latter contains an imaging control system, a hardware control system and a medical imaging device. The imaging control system being configured for communicating to the hardware control system image acquisition parameters, and the hardware control system controlling the medical imaging device according to the image acquisition parameters for performing the imaging procedure. The method according to the invention includes:

a. connecting a dynamic correction module (hereafter DCM) to the medical imaging apparatus, for example by using connectors and/or a logical connection, the medical imaging apparatus being preferentially a MRI apparatus configured for acquiring imaging raw data of the object according to a MRI procedure, wherein the DCM might comprise a software and/or a hardware component. Preferentially, the connection of the DCM to the medical imaging apparatus is a logical connection, wherein the DCM is for example a software that contains programming instructions for enabling the DCM to acquire/collect/send/receive data from the medical imaging apparatus, e.g. from a processing unit of the medical imaging apparatus, and/or from a memory, and/or from an analog-to-digital converter, and/or from another software of the medical imaging apparatus, the method according to the invention being in this case preferentially a computer implemented method;

b. automatically acquiring/collecting by the DCM through its connection to the medical imaging apparatus image acquisition parameters and/or commands defined by and in the imaging control system for performing the imaging procedure projected by the medical imaging apparatus for imaging the object, as well as data about dynamic changes or effects (hereafter "dynamic change data"), wherein the image acquisition parameters and image acquisition commands are respectively data and control commands configured for controlling the medical imaging device of the medical imaging apparatus by means of the hardware control system. The image acquisition parameters/commands defining at least one part, in particular the entire, imaging procedure (e.g., in the context of MRI, image acquisition parameters/commands might be related to real-time events like gradient pulse events, RF pulse events, RF acquisition events) and the dynamic change data being data related to the detection or measurement of a dynamic effect that might degrade the quality of the image obtained for the object by the medical imaging apparatus. Each dynamic change data containing in particular information about a motion of at least one part of the object (the part of the object defining for example a volume for which the MRI apparatus will measure an activity, e.g. a brain activity for a part or certain volume of the brain), and/or a technical change such as a drift of the magnetic field or a technically induced change of a RF pulse flip angle in case of an MRI apparatus, and/or an environmental change within the examined part or volume or the imaged object itself such as a change in field homogeneity (shim) in case of an MRI apparatus. The dynamic change data being acquired by the DCM from one or more sources, such as a field probe in case of an MR scanner and/or a respiratory belt to monitor a subject's/patient's respiration and/or a motion detection device (e.g. a camera), of the medical imaging apparatus, through the connection to the medical imaging apparatus or through a direct connection to each of the sources, wherein each source is configured for measuring/detecting at least one dynamic effect;

c. automatically determining or calculating in real time, by means of the DCM, at least one new image acquisition parameter/command from the image acquisition parameters/commands defined in the imaging control system and the dynamic change data. The new image acquisition parameter/command is preferentially one of the image acquisition parameters/commands defined in the imaging control system (called hereafter "the corresponding image acquisition parameter/command"), but optimized for the dynamic change occurring during imaging the object—in other words, it is an adapted/corrected version/value of the image acquisition parameter/command defined in the imaging control system—, while the corresponding image acquisition parameter/command defined in the imaging control system remains unchanged, i.e. while the corresponding image acquisition parameter/command defined or stored in the imaging control system remains free of any optimization/adaptation, notably in function of the dynamic change data;

d. automatically providing, by means of the DCM, the new image acquisition parameter/command to the hardware control system. Advantageously, image acquisition parameters/commands defined in the imaging control system are thus adapted or corrected in real time by the DCM in function of the dynamic change data before being processed by the hardware control system in order to perform an imaging procedure and to control the medical imaging device according to the new image acquisition parameter/command.

According to the present invention, the new image acquisition parameter/command is an image acquisition parameter/command defined in the imaging control system and optimized for the dynamic change occurring during imaging the object. The adaptation/change/correction of the image acquisition parameters/commands that define the imaging procedure is, according to the present method, free of any adaptation/change/correction of the image acquisition parameters/commands that are defined in the imaging control system, e.g. in a software or hardware of the imaging control system. The DCM according to the invention is thus capable of adapting, preferentially automatically adapting, the imaging acquisition parameters/commands in real-time in function of the dynamic change data in a manner free of any change in the execution/running of a software or hardware of the imaging control system whose purpose is the execution of the imaging procedure.

Advantageously, the present invention completely decouples the imaging control module/layer, i.e. the process controlled by programmed instructions of the software or hardware of the imaging control system for defining and controlling the imaging procedure within the imaging control system during imaging acquisition, e.g. a MR sequence in MRI, and the correction/optimization process performed by the DCM, so that it becomes possible to apply the correction/optimization performed by the DCM to any imaging procedure without or with very little additional efforts. Indeed, the DCM according to the invention contains in particular several optimization procedures/models for optimizing image acquisition parameters/commands in function of dynamic changes reported by the dynamic change data. Indeed, the DCM according to the invention may comprise in particular a memory for storing one or several models, each designed for mitigating the effect of a specific dynamic change during image acquisition, e.g. the motion of the object during image acquisition, by determining the new image acquisition parameters/commands and adapting in real time the imaging procedure of the medical imaging apparatus to the new image acquisition parameters/commands.

The present invention also concerns a DCM configured for optimizing in real time image acquisition parameters/commands of an imaging procedure performed by a medical imaging apparatus for imaging an object. The DCM contains:

a) connectors for connecting, e.g. logically and/or physically connecting, the DCM to the medical imaging apparatus, for example the connectors are logical connectors and the DCM is a software and/or comprises programming instructions stored in a memory;

b) a processing unit for processing dynamic change data and image acquisition parameters/commands;

c) a computer readable medium containing a memory for storing computer executable instructions, that, when executed, cause the processing unit to perform steps b-d previously described, the computer executable instructions containing at least one, preferentially several optimization procedures for optimizing the image acquisition parameters/commands in function of dynamic changes occurring in real time during imaging of the object by the medical imaging apparatus. Wherein preferentially each optimization procedure is configured for mitigating one or several dynamic effects.

Finally, the present invention also concerns a MRI apparatus for imaging an object, the MRI apparatus containing the DCM.

The present invention proposes thus a method and a device, the so-called DCM, that is configured for cooperating with a medical imaging apparatus like a MRI apparatus in order to correct for dynamic effects occurring during a medical imaging exam and that may impede the resulting image quality. The present invention advantageously facilitates the implementation of correction methods for different perturbing dynamic effects like motion, hardware-induced environment changes, physiological changes, etc., in a single device, i.e. said DCM, that has a unified interface for cooperating with the medical imaging device and with other devices providing said dynamic change data. Compared to prior art techniques, the present invention also avoids the requirement of separate correction of the dynamics effects, since they can all be corrected in a single step by the present invention.

Other features which are considered as characteristic for the invention are set forth in the appended claims.

Although the invention is illustrated and described herein as embodied in a method and a device for dynamic effects correction in medical imaging, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE SEVERAL VIEWS OF THE DRAWING

The single FIGURE of the drawing is a schematic illustration for illustrating a method according to the invention.

DETAILED DESCRIPTION OF THE INVENTION

The present invention will be described now by taking two specific examples of dynamic changes, respectively motion and frequency drift occurring during an examination in an MRI apparatus, in relation with the FIGURE. The two specific examples only serve as illustration of the present invention. A person of average skill in the art will recognize that the present invention applies to other dynamic changes in a similar way.

Prior art medical imaging apparatus typically contain an imaging control system 1, a hardware control system 2, and a medical imaging device 3 that interacts with the object to be imaged. The imaging control system 1 usually includes a user interface and control modules for defining an imaging procedure characterized by image acquisition parameters and commands configured for implementing the imaging procedure by the medical imaging device 3. The imaging control system 1 controls the hardware control system 2 and communicates to the latter the image acquisition parameters/commands for performing the imaging. The hardware control system 2 provides and receives information from the medical imaging device 3 in order to execute the imaging procedure defined by the image acquisition parameters/commands provided by the imaging control system 1. The present invention introduces to this known working schema a new transparent layer that is the DCM 4 which is configured for interacting at least with the imaging control system 1 and the hardware control system 2 for optimizing the imaging procedure.

In case of motion correction, a set of image acquisition parameters/commands is in particular related to the "field of view" (FOV), for example the image acquisition parameters of the set are geometric information (position and orientation) of the volume to be imaged (e.g. a part of the object to be imaged). If the examined object or at least one part of the object moves during the imaging procedure, the previously defined FOV is rendered invalid with respect to the original planning. Special devices or software modules known in the art might be used for detecting object motion, monitoring the object part under examination and updating accordingly the geometric information. Dynamic change data characterizing the detected motion of the object or of a part of the object, e.g. an object motion trajectory, is then transferred to the DCM by the special device or software module configured for detecting the object motion and with which the DCM might communicate. In this particular case, the dynamic change data comprises updated geometric information related to the FOV related to the detected motion of the imaged object. After reception of the dynamic change data, the DCM is then capable of determining new image acquisition parameters/commands related to the FOV from the dynamic change data. The new image acquisition parameters/commands allow to move the FOV of the imaging procedure so that, for example, the FOV is moved according to the measured object motion trajectory, effectively "following" the object or object part's movement with the FOV. In particular, if the medical imaging apparatus is a MRI apparatus, the newly determined image acquisition parameters/commands that will optimize the imaging procedure according to the object/object part motion are configured for adapting a rotation matrix defining the gradient coordinate system as well as adapting frequency and phase associated with excitation and demodulation imaging procedures. Finally, the new image acquisition parameters/commands are transferred or sent by the DCM 4 to the hardware control system 2 which performs the image acquisition based on the new image acquisition parameters/commands which have been optimized by the DCM 4 for the currently object/object part motion. The previously described method happens during the acquisition process of the image by the medical imaging apparatus, i.e. in real-time.

Advantageously, the DCM 4 is transparent for both the image control system 1 and the hardware control system 2, in that none of them has to be changed to implement the motion correction previously described. In other words, the DCM 4 is transparent to the parts of the imaging control system 1 previously defining the image acquisition parameters/commands as well as the parts of the imaging control system 1 controlling the hardware control system 2.

In case of frequency drift correction in an MRI apparatus, the DCM 4 is able to determine new acquisition parameters/commands configured for adapting the MRI apparatus scanner's center frequency in order to correct frequency drifts caused by technical effects or physiological activity of the imaged object part (e.g. respiration or heart beat). In this case, an acquisition parameter might be the scanner frequency, which might be in particular regularly measured by a special device or software module. Information about the measured scanner frequency might be then fed into the DCM 4 as dynamic change data. According to the present invention, the DCM 4 could comprise an optimization model correlating the measured scanner frequencies (i.e. the dynamic change data) and the acquisition parameters/commands in order to determine new acquisition parameters/commands that will adapt/correct the imaging procedure for mitigating the effects of frequency drift. Again, by using a DCM augmented by a model, the image control parameters/commands can be changed transparent to the imaging and hardware control modules or software layers. Hereby the model provides the information to relate measured frequency drifts to the corrections of the imaging parameters/commands needed to compensate those drifts.

In particular, the DCM 4 according to the present invention contains at least one interface for another software or hardware module configured for receiving dynamic change data from said software or hardware module, which might be for example a motion correction camera, and/or physiological sensors 52 like a respiration belt, and/or other sensors measuring technical dynamic effects 51 like magnetometers, and/or software modules measuring dynamic effects 53, for example software modules capable of processing specific "navigator" data acquired by the medical imaging device 3 for obtaining dynamic change data, i.e. information about a dynamic effect. The DCM 4 is configured for collecting and processing the dynamic change data provided by the above-mentioned sources of dynamic change data, for example by using an optimization model relating the received dynamic change data to the new image acquisition parameters/commands in order to correct/adapt the image acquisition parameters/commands (e.g. hardware commands) received from the imaging control system 1 and to send to the hardware control system 2 optimized image acquisition parameters/commands, i.e. the new image acquisition parameters/commands determined in real time by the DCM 4 in function of the dynamic change data.

Advantageously, the DCM 4 according to the invention might be specifically configured for correcting a single dynamic effect, another DCM 4 according to the invention being specifically dedicated to the correction of another single dynamic effect. Each DCM 4 correcting a specific dynamic effect might be replaced by another DCM 4 for correcting another specific dynamic effect or might be used together with the another DCM so that two specific dynamic effects might be corrected. A single DCM might also correct several specific dynamic effects. In particular, several DCMs might be concatenated, each of the DCMs either compensating a part of a certain effect or each DCMs correcting a distinct effect.

According to the present invention, the DCM 4 is configured for centralizing all dynamic change data related to dynamic effects that might deteriorate the image quality in order to dynamically correct acquisition parameters/commands by calculating/determining new acquisition parameters/commands. Due to the centralization, the DCM 4 is in particular able to combine information from different input sources, i.e. to combine dynamic change data acquired through different sources (e.g. a camera and another software module). Advantageously, combining information from different sources allows optimizing the correction of the imaging procedure for a specific, in particular single, dynamic effect. Indeed, complementary information might be found from the different sources.

Preferentially, each communication between the imaging control system 1 and the hardware control system 2 which are free of data related to a dynamic effect is bypassed by the DCM 4.

The invention claimed is:

1. A method for automatically and dynamically optimizing image acquisition parameters or commands of an imaging procedure performed by a medical imaging apparatus to mitigate or cancel dynamic effects perturbing an image acquisition process of an object to be imaged by the medical imaging apparatus, which comprises the steps of:
   a). connecting a dynamic correction module (DCM) to the medical imaging apparatus;
   b). automatically acquiring by the DCM dynamic change data containing dynamic changes or effects and the image acquisition parameters or commands defined by an imaging control system of the medical imaging apparatus, the imaging control system being separate from and decoupled from the DCM;
   c). automatically determining in real time, by means of the DCM, at least one new image acquisition parameter or command from the dynamic change data and the image acquisition parameters or commands defined in the imaging control system, the new image acquisition parameter or command being one of the image acquisition parameters or commands defined in the imaging control system, but optimized for a dynamic change, while the one image acquisition parameter or command defined in the imaging control system and corresponding to the new image acquisition parameter or command remaining free of any adaptation to the dynamic change data, wherein the image acquisition process being controlled by programmed instructions of the imaging control system for defining and controlling the imaging procedure during imaging acquisition, wherein a correction or optimization process performed by the DCM are completely decoupled from the imaging control system, so that the image acquisition parameters or commands defined in the imaging control system for controlling a current image acquisition remain free of any adaptation to the dynamic change data during the current image acquisition; and
   d). automatically providing, by means of the DCM, the new image acquisition parameter or command to a hardware control system controlling the medical imaging apparatus.

2. The method according to claim 1, wherein the dynamic change data are data related to a detection or measurement of a dynamic effect that might degrade a quality of an image obtained for the object by means of the medical imaging apparatus.

3. The method according to claim 1, wherein the dynamic change data contains at least one of information about a motion of at least one part of the object, a technical change of the medical imaging apparatus or parts of it, or an environmental change of an imaged volume or an imaged object/subject.

4. The method according to claim 1, wherein the image acquisition parameters or commands are defined by an imaging control system of the medical imaging apparatus for performing the imaging procedure projected by the medical imaging apparatus for imaging the object.

5. The method according to claim 1, wherein the image acquisition parameters or commands define at least one part of the imaging procedure.

6. The method according to claim 1, wherein the image acquisition parameters or commands are data/control commands configured for controlling a medical imaging device of the medical imaging apparatus by a hardware control system.

7. The method according to claim 1, wherein the medical imaging apparatus is a magnetic resonance imaging apparatus and the image acquisition parameters or commands are data/commands about at least one of a gradient pulse, a radio frequency pulse, or a radio frequency data sampling.

8. The method according to claim 1, which further comprises acquiring, via the DCM, the dynamic change data from at least one source of the medical imaging apparatus, wherein the source is configured for measuring/detecting at least one dynamic effect.

9. The method according to claim 8, which further comprises configuring the DCM to combine the dynamic change data of at least two sources for optimizing a correction of the imaging procedure for a single dynamic effect.

10. A dynamic correction module (DCM) for optimizing in real-time image acquisition parameters or commands of an imaging procedure performed by a medical imaging apparatus for imaging an object, the DCM comprising:
    connections means for connecting the DCM to the medical imaging apparatus;
    a processing unit for processing dynamic change data and the image acquisition parameters or commands received from an imaging control system of the medical imaging apparatus; and
    a computer readable medium having a memory for storing computer executable instructions, that, when executed, cause said processing unit to perform the steps of:
    automatically acquiring by the DCM the dynamic change data containing dynamic changes or effects and the image acquisition parameters or commands defined by the imaging control system of the medical imaging apparatus;
    automatically determining in real time, by means of the DCM, at least one new image acquisition parameter or command from the dynamic change data and the image acquisition parameters or commands defined in the imaging control system, the new image acquisition parameter or command being one of the image acquisition parameters or commands defined in the imaging control system, but optimized for a dynamic change, while the one image acquisition parameter or command defined in the imaging control system and corresponding to the new image acquisition parameter or command remaining free of any adaptation to the dynamic change data, wherein the image acquisition process being controlled by programmed instructions of the imaging control system for defining and controlling the imaging procedure during imaging acquisition, wherein a correction or optimization process performed by the DCM are completely decoupled from the imaging control system, so that the image acquisition parameters or commands defined in the imaging control system for controlling a current image acquisition remain free of any adaptation to the dynamic change data during the current image acquisition; and automatically providing, by means of the DCM, the new image acquisition parameter or command to a hardware control system controlling the medical imaging apparatus.

11. The DCM according to claim 10, wherein said computer executable instructions contain several optimization procedures/models for optimizing the image acquisition parameters or commands in dependence on dynamic changes occurring in real-time during imaging of the object by means of the medical imaging apparatus, wherein each optimization procedure is configured for mitigating one dynamic effect.

12. The DCM according to claim 10, wherein the DCM is configured for combining the dynamic change data acquired from at least one source of the medical imaging apparatus, wherein the source is configured for measuring/detecting at least one dynamic effect, the DCM being further configured for combining the dynamic change data of at least two sources for optimizing a correction of the imaging procedure for a single dynamic effect.

13. A magnetic resonance imaging apparatus for imaging an object, comprising:
  a hardware control system;
  an imaging control system;
  a dynamic correction module (DCM) for optimizing in real-time image acquisition parameters or commands of an imaging procedure performed by the magnetic resonance imaging apparatus for imaging the object, the DCM containing:
    connections means for connecting said DCM to other parts of the magnetic resonance imaging apparatus;
    a processing unit for processing dynamic change data and the image acquisition parameters or commands received from said imaging control system; and
    a computer readable medium having a memory for storing computer executable instructions, that, when executed, cause said processing unit to perform the steps of:
      automatically acquiring by the DCM the dynamic change data containing dynamic changes or effects and the image acquisition parameters or commands defined by said imaging control system;
      automatically determining in real time, by means of the DCM, at least one new image acquisition parameter or command from the dynamic change data and the image acquisition parameters or commands defined in the imaging control system, the new image acquisition parameter or command being one of the image acquisition parameters or commands defined in the imaging control system, but optimized for a dynamic change, while the one image acquisition parameter or command defined in the imaging control system and corresponding to the new image acquisition parameter or command remaining free of any adaptation to the dynamic change data, wherein the imaging procedure being controlled by programmed instructions of said imaging control system for defining and controlling the imaging procedure during imaging acquisition, wherein a correction or optimization process performed by said DMC are completely decoupled from said imaging control system, so that the image acquisition parameters or commands defined in said imaging control system for controlling a current image acquisition remain free of any adaptation to the dynamic change data during the current image acquisition; and
      automatically providing, by means of the DCM, the new image acquisition parameter or command to said hardware control system.

* * * * *